United States Patent [19]

Faas, Jr. et al.

[11] Patent Number: 5,098,693

[45] Date of Patent: Mar. 24, 1992

[54] ANTI-IRRITANT SPRAY FOR USE WITH CAST AND METHOD OF APPLICATION

[75] Inventors: Leonard A. Faas, Jr., Yorba Linda; Leonard A. Faas, III, Diamond Bar; William T. Spaeth, Yorba Linda; W. Kenneth Lim, Jr., Fullerton, all of Calif.

[73] Assignee: Cast Blast, Yorba Linda, Calif.

[21] Appl. No.: 697,513

[22] Filed: Apr. 29, 1991

Related U.S. Application Data

[63] Continuation of Ser. No. 384,032, Jul. 21, 1989, abandoned, which is a continuation of Ser. No. 106,685, Oct. 8, 1987, abandoned.

[51] Int. Cl.⁵ .............................................. A61L 9/04
[52] U.S. Cl. ........................................ 424/45; 424/46; 424/47; 424/DIG. 5
[58] Field of Search ............... 424/45, 46, 47, DIG. 5

[56] References Cited

U.S. PATENT DOCUMENTS

| | | | |
|---|---|---|---|
| 3,024,787 | 3/1962 | Birch et al. | 128/203 |
| 3,367,332 | 2/1968 | Groves | 128/268 |
| 3,957,994 | 5/1976 | Schroer | 424/253 |
| 4,034,077 | 7/1977 | Hill et al. | 424/69 |
| 4,239,781 | 12/1980 | Edwards | 424/342 |
| 4,350,605 | 9/1982 | Hughett | 252/305 |
| 4,512,987 | 4/1985 | Schindlery | 514/171 |
| 4,778,674 | 10/1988 | Gupte et al. | 424/46 |
| 4,778,774 | 10/1988 | Gupte et al. | 424/45 |

FOREIGN PATENT DOCUMENTS 1578989  8/1969  France .

Primary Examiner—Patrick J. Ryan
Attorney, Agent, or Firm—Gary M. Anderson

[57] ABSTRACT

This invention concerns a novel method for eliminating skin irritation or "itching" within a cast by means of applying an anti-irritant aerosol spray to the skin within the cast. The anti-irritant spray includes talc and triclosan. The spray may also include isopropyl myristate and a fragrance additive as well as trichlorotrifluoroethane and SD alcohol 40.

19 Claims, No Drawings

ANTI-IRRITANT SPRAY FOR USE WITH CAST AND METHOD OF APPLICATION

This is a continuation of copending application Ser. No. 07/384,032 filed on July 21, 1989, is now abandoned, which is a continuation of application Ser. No. 106,685, filed Oct. 8, 1987.

FIELD OF INVENTION

This invention relates to the field of anti-irritants used to relieve skin irritation within temporarily enclosed areas of the body, such as areas enclosed within a cast. In particular, the subject invention relates to anti-irritants which can be applied to the skin within an enclosure such as a cast via an aerosol spray carrier.

BACKGROUND OF INVENTION

It is known to apply compounds to the skin to alleviate skin inflammation. These compounds may be applied to the skin through a variety of carriers such as gels, foam, aerosol or liquid. Examples of such compounds and their method of application are disclosed in Schroer, U.S. Pat. No. 3,957,994; Hill et al., U.S. Pat. No. 4,034,077; Edwards, U.S. Pat. No. 4,239,781; and Schindlery, U.S. Pat. No. 4,512,987. The compounds disclosed in these patents may be categorized as medicinal or pharmaceutical compounds. They are utilized to treat various types of actual skin inflammation, abrasions or flaking.

It is also known in the art to apply powders to the skin to absorb the moisture which forms on the skin. This in turn may eliminate skin irritation or the "itching" sensation caused by the build up of moisture. Powders commonly used and known are talc or baby powders sold under the registered trademark JOHNSON & JOHNSON and common corn starch. These powders as well as the anti-inflammation compounds are commonly applied topically to exposed area of the skin.

A problem exists, however, in relieving the skin irritation which frequently develops in situations in which a area of the skin is enclosed for extended periods of time. This most frequently occurs with casts which enclose areas of the skin for varying extended periods of time necessary for broken bones to heal. Due to the nature of the normal or traditional cast, the affected skin area remains enclosed within the cast for extended periods during the healing process. Moisture from the skin builds up over time, resulting in a skin irritation or "itching" sensation and at times an unpleasant smell or odor. Prior attempts or methods of eliminating the "itching" sensation within a cast have been limited to the shaking or sprinkling of a dry talc powder or corn starch down the cast in an effort to cause the powder to reach the irritated skin area or attempting to scratch the "itching" area by inserting thin elongated elements down the cast. These methods of alleviating the "itching" sensation have proven to be ineffective.

A need therefore exists for a method of eliminating skin irritation or "itching" within an enclosed area such as a cast.

A need also exists for a method of reducing the formation of skin odor or bacteria within a cast.

SUMMARY OF INVENTION

The subject invention comprises the novel application of an anti-moisture mixture within a cast by means of an aerosol spray. In this form the anti-moisture mixture is applied as a liquid slurry within the area enclosed by the cast. Prior teaching has been to avoid the introduction of a liquid or moisture within the area enclosed by the cast. Thus, prior efforts to eliminate the "itching" sensation have been limited to the application of dry powders. The anti-moisture mixture contains a moisture absorbing agent suspended in the carrier as well as an anti-bacterial preservative agent which is dissolved in the carrier which also provides a cooling sensation when applied to the skin. The mixture is applied to the area which is experiencing the "itching" sensation under pressure via a traditional aerosol dispenser utilizing an elongated flexible applicator nozzle to enable the anti-moisture mixture to be applied within the confines of a cast. The mixture reduces or helps to eliminate the "itching" sensation or irritation by absorbing the moisture in the area. Other ingredients in the mixture provide a cooling sensation to the skin. The aerosol propellants and the mixture carriers are evaporated by the body heat within the cast, thereby preventing any moisture build-up as a result of the application of the aerosol spray itself.

DETAILED DESCRIPTION

A problem frequently experienced by individuals who are required to wear a cast or other semi-permanent, non-removable enclosure over a portion of their body is the development of an "itching" sensation or irritation on the skin within the cast. This sensation is the result of moisture accumulation, normally through perspiration, within the cast, which moisture is not readily evaporated or dried from the skin due to the particular area of the skin being enclosed within the cast. The enclosure of the skin area by the cast prohibits the circulation of air over the skin area to assist in the evaporation of the moisture.

As indicated, wearers of a cast over a portion of their body have previously been limited to trying to apply a dry talcum powder or corn starch mixture to the affected area by attempting to pour or sprinkle the powder down the limited space between the cast and the skin. This has proven to be ineffectual.

The applicants have discovered that the "itching" sensation or skin irritation attendant with the long term wearing of a cast or other body enclosure can be eliminated through the application of an aerosol spray containing a mixture of talc, triclosan, silica, trichlorotrifluoroethane, isopropyl myristate, SD alcohol 40 and, if desired, a fragrance additive. A propellant is utilized with the aerosol spray.

The talc acts to absorb any existing moisture within the cast as well as inhibit the build-up or accumulation of any additional moisture by absorbing the additional moisture as it is formed. The amount of talc may vary from 2% to 20% of the mixture with the preferred amount being approximately 3.0%. Other suitable moisture absorbants such as corn starch may be substituted for the talc.

To prevent the talc from caking or settling within the aerosol can, a small amount of silica is added to the mixture. The concentration of silica may vary from 1% to 10% of the mixture with the preferred amount of silica being approximately 1.2%. The talc is suspended in one of a variety of suitable carriers known in the art. In the preferred embodiment, the carrier includes a mixture of trichlorotrifluoroethane and SD alcohol 40. The mixture of trichlorotrifluoroethane and SD alcohol 40 may vary from 10% to 90% of the total aerosol mixture with the preferred embodiment comprising approximately 54.5%. In the preferred embodiment, the ratio of trichlorotrifluoroethane to SD alcohol 40 is approximately 2:1. Alternate carriers such as 1,1,1 trichloroethane and isopropyl alcohol may be substituted for the trichlorotrifluoroethane and SD alcohol 40.

During the application of the aerosol mixture to the skin, the trichlorotrifluoroethane and SD alcohol 40 provide a "cooling" sensation on the skin, thereby aiding in providing a quick relief to the "itching" sensation.

Also included in the aerosol mixture is isopropyl myristate which serves to provide a soothing, silky feel to the skin. This serves to eliminate that "itching" feeling present within the cast. The concentration of isopropyl myristate may vary from 0.5% to 5% of the mixture, with the preferred concentration being approximately 1.2%. The isopropyl myristate also acts to help keep the talc suspended in the mixture.

Another problem encountered with the long term wearing of a cast is the build-up of unpleasant odors which are formed within the cast by bacteria in contact with the moist skin. To prevent this, an anti-bacterial agent such as triclosan is included. Triclosan is a well known anti-bacterial agent. The concentration of triclosan may vary from 0.01% to 2.0%, with a concentration of approximately 0.09% being the preferred amount. A fragrance additive may also be included to counteract the odor build up. The concentration of fragrance may vary between 0% and 3%, with 0.03% being the preferred concentration.

The above described anti-irritant, anti-moisture mixture is applied via an aerosol spray. The spray may use any readily available and known fluorocarbon propellant, one suitable propellant mixture being hydrochlorofluorocarbon 22 and dimethylether. The propellant mixture constitutes approximately 40% of the total mixture, the concentration of hydrochlorofluorocarbon 22 varying from 5% to 50%, with the preferred concentration being approximately 12%. The concentration of dimethylether may vary from 0% to 40%, with the preferred concentration being approximately 28%. Alternate propellants such as butane, isobutane or propane may also be utilized. Further, non-fluorocarbon propellants may be utilized. Various suitable non-fluorocarbon propellant will be known to those skilled in the art.

The "anti-itch" spray is packaged in a conventional aerosol spray can, utilizing a standard push button-type spray nozzle. Spray cans and nozzles of this type are well known in the art. The spray is applied to the affected skin area by means of an elongated, flexible applicator nozzle which is attached to the normal aerosol can nozzle. The elongated applicator nozzle is inserted down inside the cast until the opening at the end of the nozzle is adjacent to the affected skin area. The individual then simply pushes the aerosol can spray button causing the spray to be applied to the skin. As it is applied, the spray provides a soothing sensation over the affected area. The talc acts to absorb any existing moisture. The aerosol propellants and the spray carriers evaporate as a result of the heat generated from the person's body. This leaves the talc and triclosan deposited on the skin to absorb any additional moisture as it is formed, as well as inhibit the formation of any odor.

The spray can be applied inside the cast without causing the cast to become soggy or saturated with moisture.

Having thus described one embodiment of the invention in detail, it is to be understood that numerous equivalents and alterations which do not depart from the invention will be apparent to those skilled in the art, given the teaching herein. Thus, the invention is not to be limited to the above description but is to be of the full scope of the appended claims.

What is claimed:

1. An anti-irritant spray for use in eliminating skin irritation within a cast including a moisture absorbing agent and an anti-bacterial agent, wherein said moisture absorbing agent is talc, having a concentration of 2% to 20% and said anti-bacterial agent is triclosan, having a concentration of 0.01% to 2%.

2. The anti-irritant spray of claim 1 wherein the moisture absorbing agent is corn starch.

3. An anti-irritant spray for use in eliminating skin irritation within a cast including 2% to 20% talc and 0.01% to 2% triclosan.

4. An anti-irritant spray for use in eliminating skin irritation within a cast including talc, having a concentration of 2% to 20%, triclosan, having a concentration of 0.01% to 2%, and trichlorotrifluoroethane and SD alcohol 40.

5. The anti-irritant spray of claim 4 wherein the concentration of trichlorotrifluoroethane ranges from 10% to 50%.

6. The anti-irritant spray of claim 4 wherein the concentration of SD alcohol 40 ranges from 10% to 50%.

7. The anti-irritant spray of claim 4 which includes isopropyl myristate ranging in concentration from 0.5% to 5%.

8. The anti-irritant spray of claim 4 which includes silica ranging in concentration from 1% to 10%.

9. The anti-irritant spray of claim 6 which includes a fragrance additive ranging in concentration from 0% to 3%.

10. The anti-irritant spray of claim 6 which includes hydrochlorofluorocarbon 22 having a concentration ranging from 5% to 50% and dimethylether having a concentration ranging from 0% to 40%.

11. An anti-irritant spray for use in eliminating skin irritation within a cast containing talc in the range of 2% to 20%, triclosan in the range of 0.01% to 2%, trichlorotrifluoroethane in the range of 10% to 50%, SD alcohol 40 in the range of 10% to 50%, isopropyl myristate in the range of 0.05% to 5%, silica in the range of 1% to 10% and a fragrance additive in the range of 0% to 3%.

12. A method for eliminating skin irritation within a cast comprising the application of an aerosol anti-irritant spray, said spray including talc and triclosan, to the skin within a cast via an elongated, flexible applicator nozzle.

13. The method of claim 12 wherein the anti-irritant spray contains 2% to 20% talc.

14. The method of claim 12 wherein the anti-irritant spray contains 0.01% to 2% triclosan.

15. The method of claim 12 wherein the anti-irritant spray contains 0.05% to 5% isopropyl myristate.

16. The method of claim 12 wherein the anti-irritant spray contains 10% to 50% trichlorotrifluoroethane and 10% to 50% SD alcohol 40.

17. The method of claim 12 wherein the anti-irritant spray contains 0% to 3% of a fragrance additive.

18. The method of claim 16 wherein the anti-irritant spray contains 1% to 10% silica.

19. A method for eliminating skin irritation within a cast comprising the application of an aerosol anti-irritant spray to the skin within a cast via an elongated, flexible applicator nozzle wherein the anti-irritant spray contains talc in the range of 2% to 20%, triclosan in the range of 0.01% to 2%, trichlorotrifluoroethane in the range of 10% to 50%, SD alcohol 40 in the range of 10% to 50%, isopropyl myristate in the range of 0.05% to 5%, silica in the range of 1% to 10% and a fragrance additive in the range of 0% to 3%.

* * * * *